(12) United States Patent
Schmidt et al.

(10) Patent No.: US 10,083,786 B2
(45) Date of Patent: *Sep. 25, 2018

(54) DUAL DOUBLE HELIX CONDUCTORS WITH LIGHT SOURCES

(71) Applicant: Medical Energetics Ltd., Galway (IE)

(72) Inventors: David G. Schmidt, Poway, CA (US); Terrence S. McGrath, San Diego, CA (US)

(73) Assignee: MEDICAL ENERGETICS LTD., Galway (IE)

( * ) Notice: Subject to any disclaimer, the term of this patent is extended or adjusted under 35 U.S.C. 154(b) by 298 days.

This patent is subject to a terminal disclaimer.

(21) Appl. No.: 15/014,484

(22) Filed: Feb. 3, 2016

(65) Prior Publication Data
US 2016/0247617 A1 Aug. 25, 2016

Related U.S. Application Data

(60) Provisional application No. 62/176,498, filed on Feb. 20, 2015.

(51) Int. Cl.
| A61N 2/02 | (2006.01) |
| H01F 7/20 | (2006.01) |
| A61N 2/00 | (2006.01) |
| A61N 5/06 | (2006.01) |
| H01F 5/02 | (2006.01) |
| A61N 5/067 | (2006.01) |

(52) U.S. Cl.
CPC ............... *H01F 7/20* (2013.01); *A61N 2/002* (2013.01); *A61N 2/02* (2013.01); *A61N 5/0613* (2013.01); *H01F 5/02* (2013.01); *A61N 2005/067* (2013.01); *A61N 2005/0643* (2013.01); *A61N 2005/0651* (2013.01); *A61N 2005/0662* (2013.01); *A61N 2005/0667* (2013.01)

(58) Field of Classification Search
CPC ...... A61N 2/00–2/12; H01F 5/00–5/06; H01F 7/06–7/206
See application file for complete search history.

(56) References Cited

U.S. PATENT DOCUMENTS

| 1,898,661 A | 2/1933 | Hagen |
| 2,035,274 A | 3/1936 | Mougey |
| 2,297,454 A | 9/1942 | Berger |
| 2,850,666 A | 9/1958 | Brewer |
| 3,037,175 A | 5/1962 | Ruthroff |
| 3,066,295 A | 11/1962 | Krause |
| 3,519,964 A | 7/1970 | Chorney |
| 3,588,689 A | 6/1971 | Crawford |
| 3,683,393 A | 8/1972 | Self |

(Continued)

FOREIGN PATENT DOCUMENTS

| GB | 479841 A | 2/1938 |
| GB | 2480610 A | 11/2011 |

(Continued)

*Primary Examiner* — Thaddeus Cox
(74) *Attorney, Agent, or Firm* — ARC IP Law, PC; Joseph J. Mayo (57) ABSTRACT

An electrical system including multiple bodies having an underlying structure resembling a double helix may be arranged and used, to produce useful electromagnetic effects for various applications, including therapy and the promotion of growth in organisms and organic matter.

30 Claims, 8 Drawing Sheets

(56) References Cited

U.S. PATENT DOCUMENTS

| | | | |
|---|---|---|---|
| 3,760,812 A | 9/1973 | Timm |
| 3,774,452 A | 11/1973 | Tullos |
| 4,131,759 A | 12/1978 | Felkel |
| 4,229,676 A | 10/1980 | Manoly |
| 4,266,532 A | 5/1981 | Ryaby |
| 4,439,702 A | 3/1984 | Belikov |
| 4,489,276 A | 12/1984 | Yu |
| 4,832,051 A | 5/1989 | Jarvik |
| 4,989,617 A | 2/1991 | Memberg |
| 5,077,934 A | 1/1992 | Liboff |
| 5,079,458 A | 1/1992 | Schuster |
| 5,173,669 A | 12/1992 | Manoly |
| 5,182,537 A | 1/1993 | Thuis |
| 5,339,061 A | 8/1994 | Reick |
| 5,359,340 A | 10/1994 | Yokota |
| 5,366,493 A | 11/1994 | Scheiner |
| 5,464,456 A | 11/1995 | Kertz |
| 5,654,723 A | 8/1997 | Craven |
| 5,819,467 A | 10/1998 | Zucker |
| 5,851,206 A | 12/1998 | Guglielmi |
| 5,892,480 A | 4/1999 | Killen |
| 5,909,165 A | 6/1999 | Leupold |
| 5,954,630 A | 9/1999 | Masaki |
| 5,977,932 A | 11/1999 | Robinson |
| 6,005,462 A | 12/1999 | Myers |
| 6,169,523 B1 | 1/2001 | Ploussios |
| 6,239,760 B1 | 5/2001 | VanVoorhies |
| 6,300,920 B1 | 10/2001 | Pertl |
| 6,520,986 B2 | 2/2003 | Martin |
| 6,552,530 B1 | 4/2003 | Vaiser |
| 6,770,023 B2 | 8/2004 | Vaiser |
| 6,921,042 B1 | 7/2005 | Goodzeit |
| 6,978,179 B1 | 12/2005 | Flagg |
| 7,148,783 B2 | 12/2006 | Parsche |
| 7,154,368 B2 | 12/2006 | Sweeney |
| 7,375,449 B2 | 5/2008 | Butterfield |
| 8,323,328 B2 | 12/2012 | Martin |
| 8,463,407 B2 | 6/2013 | Bulkes |
| 8,652,023 B2 | 2/2014 | Schmidt |
| 8,653,925 B2 | 2/2014 | Schmidt |
| 8,749,333 B2 | 6/2014 | Schmidt |
| 8,919,035 B2 | 12/2014 | Schmidt |
| 8,961,384 B2 | 2/2015 | Schmidt |
| 9,030,283 B2 | 5/2015 | Schmidt |
| 9,370,667 B2 | 6/2016 | Schmidt |
| 9,406,421 B2 | 8/2016 | Schmidt |
| 9,504,845 B2 | 11/2016 | Schmidt |
| 2003/0011527 A1 | 1/2003 | Kokorin |
| 2003/0095022 A1* | 5/2003 | Boynton ................ A61N 2/02 335/299 |
| 2003/0158585 A1 | 8/2003 | Burnett |
| 2003/0169132 A1 | 9/2003 | Vaiser |
| 2003/0230427 A1 | 12/2003 | Gareis |
| 2005/0094989 A1 | 5/2005 | Halpin |
| 2005/0121396 A1 | 6/2005 | Kosakewich |
| 2005/0228209 A1 | 10/2005 | Schneider et al. |
| 2007/0024520 A1 | 2/2007 | Preble |
| 2007/0258329 A1 | 11/2007 | Winey |
| 2008/0161884 A1 | 7/2008 | Chandler |
| 2008/0266203 A1 | 10/2008 | Rossetto |
| 2009/0083969 A1 | 4/2009 | Meinke |
| 2009/0206974 A1 | 8/2009 | Meinke |
| 2009/0260849 A1 | 10/2009 | Cardas |
| 2010/0005711 A1 | 1/2010 | McNeff |
| 2010/0057655 A1 | 3/2010 | Jacobson |
| 2010/0113862 A1 | 5/2010 | Kotowich |
| 2010/0114280 A1 | 5/2010 | Hill |
| 2010/0121131 A1* | 5/2010 | Mathes ............ A61H 23/0236 600/14 |
| 2010/0152811 A1 | 6/2010 | Flaherty |
| 2010/0179630 A1 | 7/2010 | Williams |
| 2012/0101366 A1 | 4/2012 | Ruohonen |
| 2012/0143285 A1 | 6/2012 | Wang |
| 2012/0223800 A1 | 9/2012 | Schmidt |
| 2013/0192129 A1 | 8/2013 | Schmidt |
| 2013/0211181 A1 | 8/2013 | Schmidt |
| 2013/0274542 A1* | 10/2013 | Volo .................... A61N 1/40 600/13 |
| 2013/0285782 A1 | 10/2013 | Schmidt |
| 2014/0097925 A1 | 4/2014 | Schmidt |
| 2014/0100412 A1 | 4/2014 | Schmidt |
| 2014/0218149 A1 | 8/2014 | Schmidt |
| 2014/0371514 A1 | 12/2014 | Schmidt |
| 2015/0119630 A1 | 4/2015 | Schmidt |
| 2015/0119631 A1 | 4/2015 | Schmidt |
| 2015/0119632 A1 | 4/2015 | Schmidt |
| 2015/0157871 A1 | 6/2015 | Schmidt |
| 2015/0283393 A1 | 10/2015 | Schmidt |
| 2015/0283394 A1 | 10/2015 | Schmidt |
| 2016/0172088 A1 | 6/2016 | Schmidt |
| 2016/0172101 A1 | 6/2016 | Schmidt |
| 2016/0247614 A1 | 8/2016 | Schmidt |
| 2016/0365186 A1 | 12/2016 | Schmidt |

FOREIGN PATENT DOCUMENTS

| | | |
|---|---|---|
| WO | 2012118971 A2 | 9/2012 |
| WO | 2013112810 A1 | 8/2013 |
| WO | 2013123009 A1 | 8/2013 |

* cited by examiner

DUAL DOUBLE HELIX CONDUCTORS WITH LIGHT SOURCES

FIELD OF THE INVENTION

The invention relates to bodies that include helically wound runners around which one or more conductive wires are wound, devices including such bodies, and/or (electrical) systems including such bodies. A body with one or more wound conductive wires may be referred to as a coil. Devices and systems may include two or more coils. The invention further relates to the manufacture of such bodies, devices, and/or systems. The invention further relates to methods of operation of such devices and systems, and applications thereof. The invention further relates to such devices and/or systems configured to provide therapy to patients by using electromagnetic effects such as electromagnetic fields. The invention further relates to such devices and/or systems configured to promote growth in organisms and organic matter by using electromagnetic effects such as electromagnetic fields.

BACKGROUND OF THE INVENTION

It is known that spirally wound electrical conductors may exhibit certain electromagnetic properties and/or electromagnetic effects. For example, it is known that an electromagnetic coil may act as an inductor and/or part of a transformer, and has many established useful applications in electrical circuits. Multiple coils may be used to exploit an electromagnetic field and/or other electromagnetic effect that is created when, e.g., one or more active current sources and/or one or more light sources are operatively coupled to the coils or operated in conjunction.

SUMMARY

One aspect of the invention relates to a system comprising one or more bodies, one or more current sources, one or more sources of electromagnetic radiation, and/or one or more conductive wires. Individual bodies may include two or more intertwined helically wound runners. A first runner may be coupled to the second runner by struts and/or held in position through other support structures. Individual runners may have a helical shape. Individual bodies may be arranged in toroidal shapes. One or more conductive wires may be spirally wound around at least one runner.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
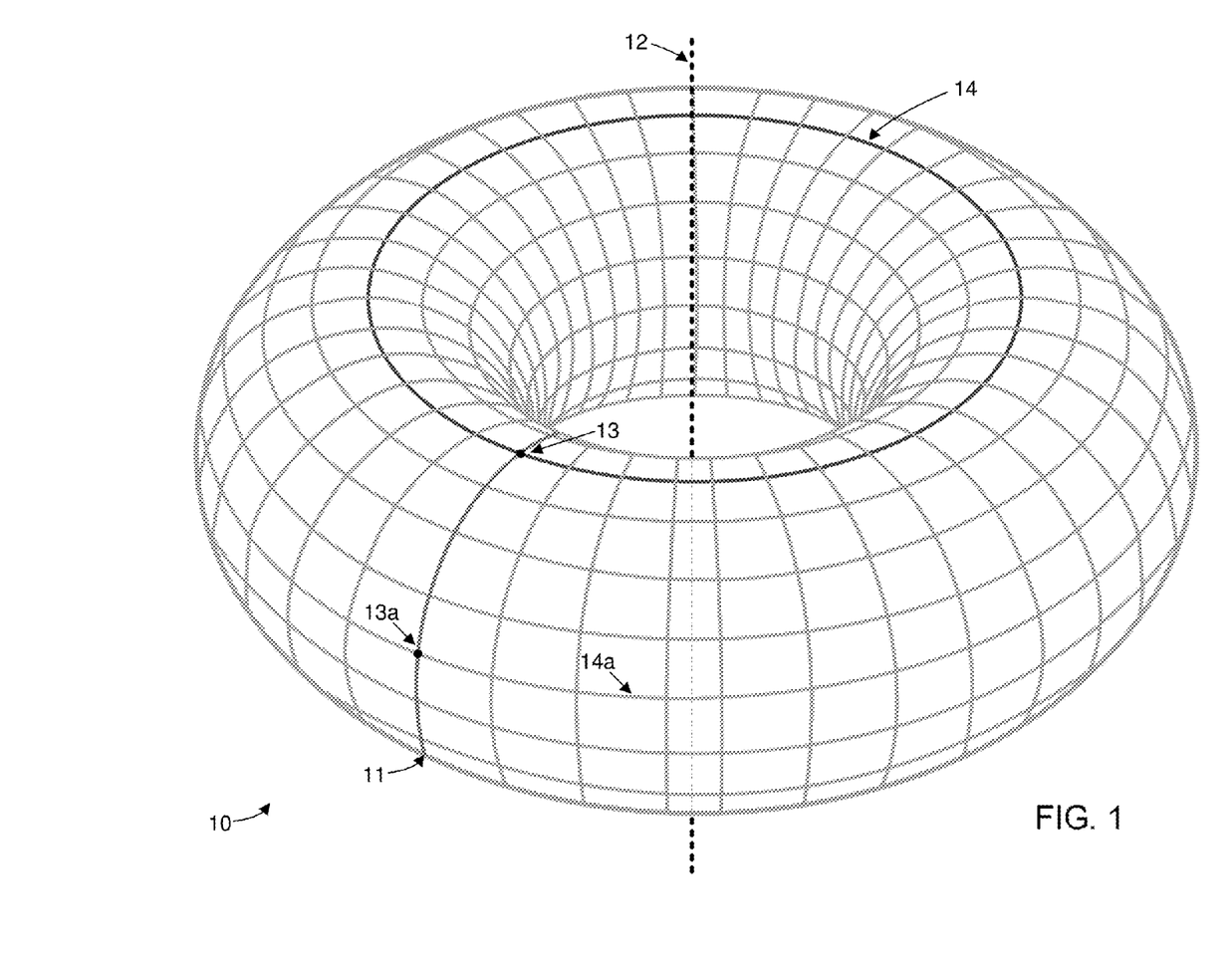
FIG. 1 illustrates a toroidal shape.

FIG. 1 illustrates a toroidal shape 10. A toroidal shape such as shape 10 may be formed by revolving a circle 11 (partially shown in FIG. 1) in three-dimensional space about an axis 12 that is coplanar with circle 11. Toroidal shape 10 may be informally referred to as a donut shape or a bagel shape. Axis 12 may be said to go through the donut hole of toroidal shape 10. The surface of toroidal shape 10 may be a torus. Circle 11 may include a point 13, a point 13a, and other points. As circle 11 is revolved to form toroidal shape 10, point 13 describes a circle 14 that defines a plane. This plane is perpendicular to axis 12. Different points on circle 11 describe different circles on the surface of toroidal shape 10. As circle 11 is revolved, point 13a describes a circle 14a that defines a plane. This plane bisects toroidal shape 10 and is perpendicular to axis 12. In some implementations, for a particular point 13a and a particular circle 14a, the defined plane bisects toroidal shape 10 into two similar, congruent, and/or isometric halves, e.g. as if cutting a bagel in half such that the surface area of the cut has the shape of a mathematical ring or annulus (i.e. a first circle with a relatively smaller radius completely inside a second circle with a relatively larger radius, with both circles being concentric, the term "relatively" being used to relate the first circle and the second circle).

Figure 2:
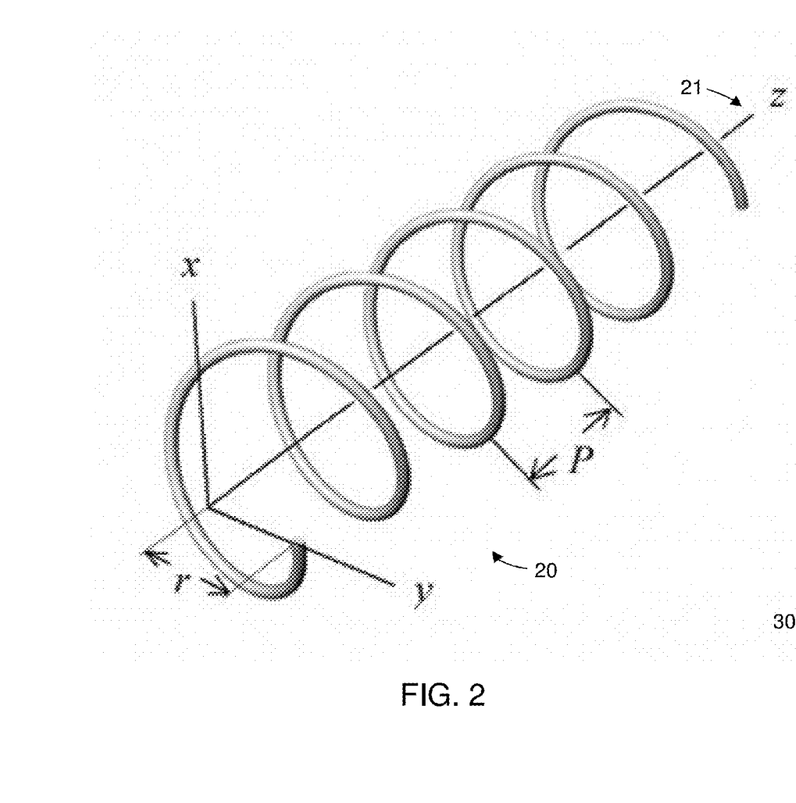
FIG. 2 illustrates a helical shape.

FIG. 2 illustrates a helical shape 20. A helical shape such as shape 20 may be formed by a curve in three-dimensional space that has the property that the tangent line at any point makes a constant angle with a fixed line called an axis 21 (labeled "z" in FIG. 2, and perpendicular to both the "x" and "y" axes in FIG. 2). The width of one complete helix turn or revolution, measured parallel to axis 21, is called pitch (labeled "P" in FIG. 2). The shortest distance from helical shape 20 to axis 21 is called the radius (labeled "r" in FIG. 2). Helical shape 20 may have a constant radius, and be referred to as a circular helix.

Figure 3:
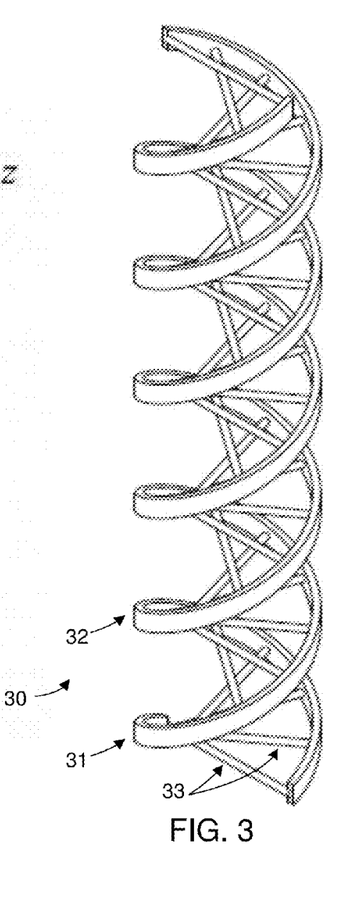
FIG. 3 illustrates an exemplary body including two intertwined helically wound runners in the shape of a double helix, the runners being coupled and/or supported by struts.

FIG. 3 illustrates an exemplary body 30 including two intertwined helically wound runners, a first runner 31 and a second runner 32, in the shape of a double helix, the runners being coupled and/or supported by struts 33. In some implementations, the runners of a double helix may be supported by other support structures. The double helix may include two helical shapes, each of which may be similar to helical shape 20 as shown in FIG. 2. It is noted that the shape of body 30 resembles the general shape of deoxyribonucleic acid (DNA), e.g. a double helix. A helical shape may have a straight axis, as shown in FIG. 2 and FIG. 3, or a curved axis as shown in, e.g., FIG. 4.

Figure 4:
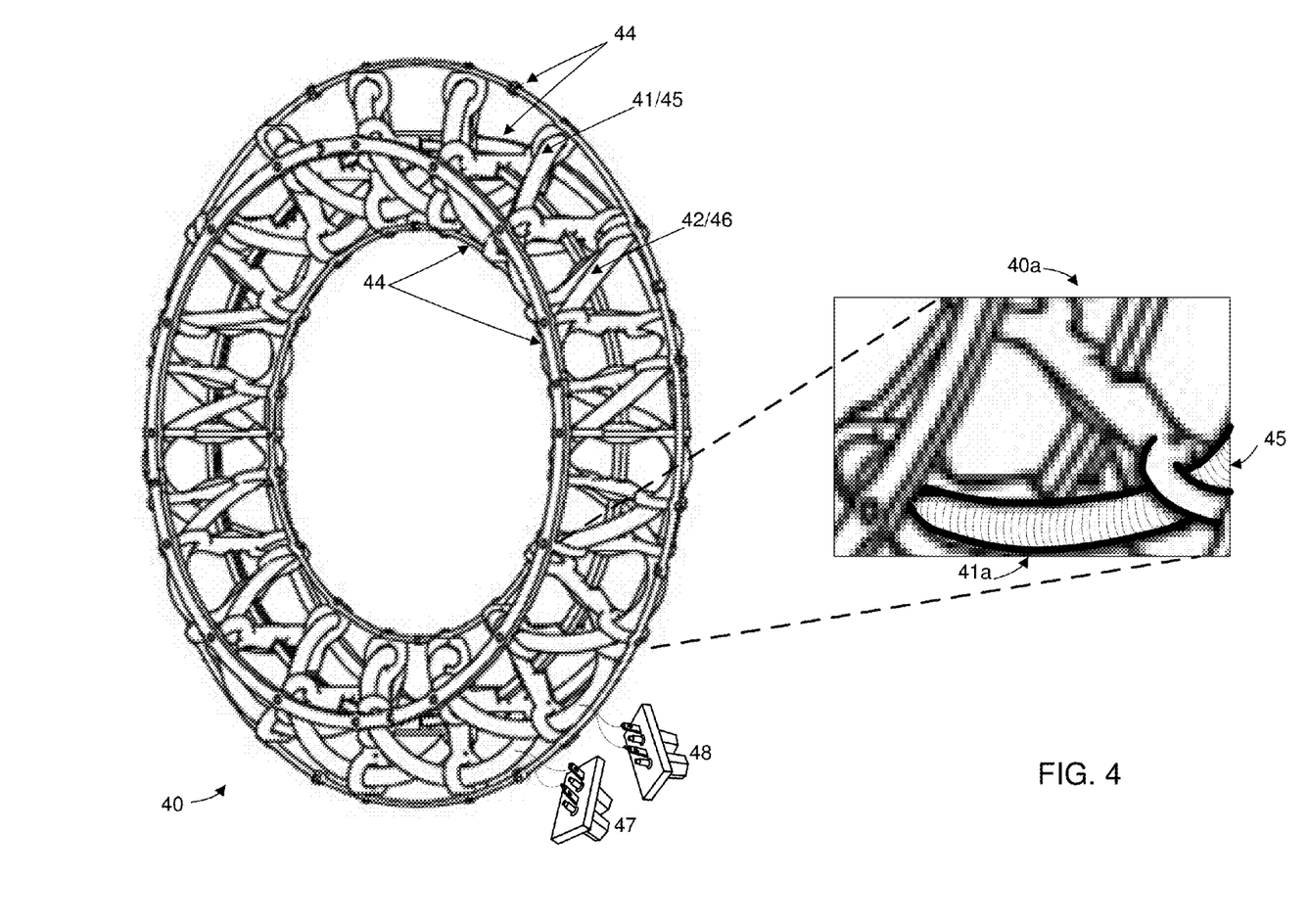
FIG. 4 illustrates an exemplary body including two intertwined helically wound runners, the body arranged to form a toroidal shape.

FIG. 4 illustrates an exemplary body 40 including two intertwined helically wound runners, a first runner 41 and a second runner 42, in the shape of a double helix, the body 40 being arranged to form a toroidal shape which may be similar to toroidal shape 10 as shown in FIG. 1. Body 40 may be arranged such that the axis of the double helix is not straight but curved, e.g. in a circle or oval. The runners of body 40 may be supported by support structures 44. As shown in a view 40a that illustrates a magnified section of body 40, which includes a section 41a of runner 41, a wire 45 may be wound around runner 41. Wire 45 may be conductive. Wire 45 may be too fine to be visible in a figure without magnification. A wire such as wire 45 may be insulated, uninsulated, or partially insulated and partially uninsulated, as may any wire listed in any figure included in this description. As used herein, a "wire" may include a set of twisted wires (which may interchangeably be referred to as a "twisted wire"), including but not limited to a set of two twisted wires. A wire 46 may be wound around runner 42 in a manner similar to wire 45 and runner 41. A connector 47 may be electrically coupled to twisted wire 45. For example, as shown in FIG. 4, both ends of twisted wire 45 may be electrically coupled to connector 47. A connector 48 may be electrically coupled to twisted wire 46. For example, as shown in FIG. 4, both ends of twisted wire 46 may be electrically coupled to connector 48. One or more power sources and/or current sources (not shown in FIG. 4) may be electrically coupled to connector 47 and/or connector 48 to supply current to twisted wire 45 and/or twisted wire 46, respectively, such that an electromagnetic effect (e.g. an electromagnetic field) is created around and/or near body 40. In some implementations, a system may include multiple bodies that are similar to body 40. Such a system may be configured to generate and/or create an electromagnetic effect around and/or near the multiple bodies. By virtue of this electromagnetic effect, such a system may be used to provide therapy, e.g. to patient, promote growth, and/or be used for other applications.

In some implementations, body 40 may be constructed such that its diameter is about 4 inches, about 6 inches, about 8 inches, about 10 inches, about 1 foot, about 18 inches, about 2 feet, about 30 inches, about 3 feet, about 4 feet, about 5 feet, about 6 feet, about 7 feet, about 8 feet, about 9 feet, about 10 feet, and/or other sizes. In some implementations, body 40 may have a diameter of about 20 inches.

Figure 5:
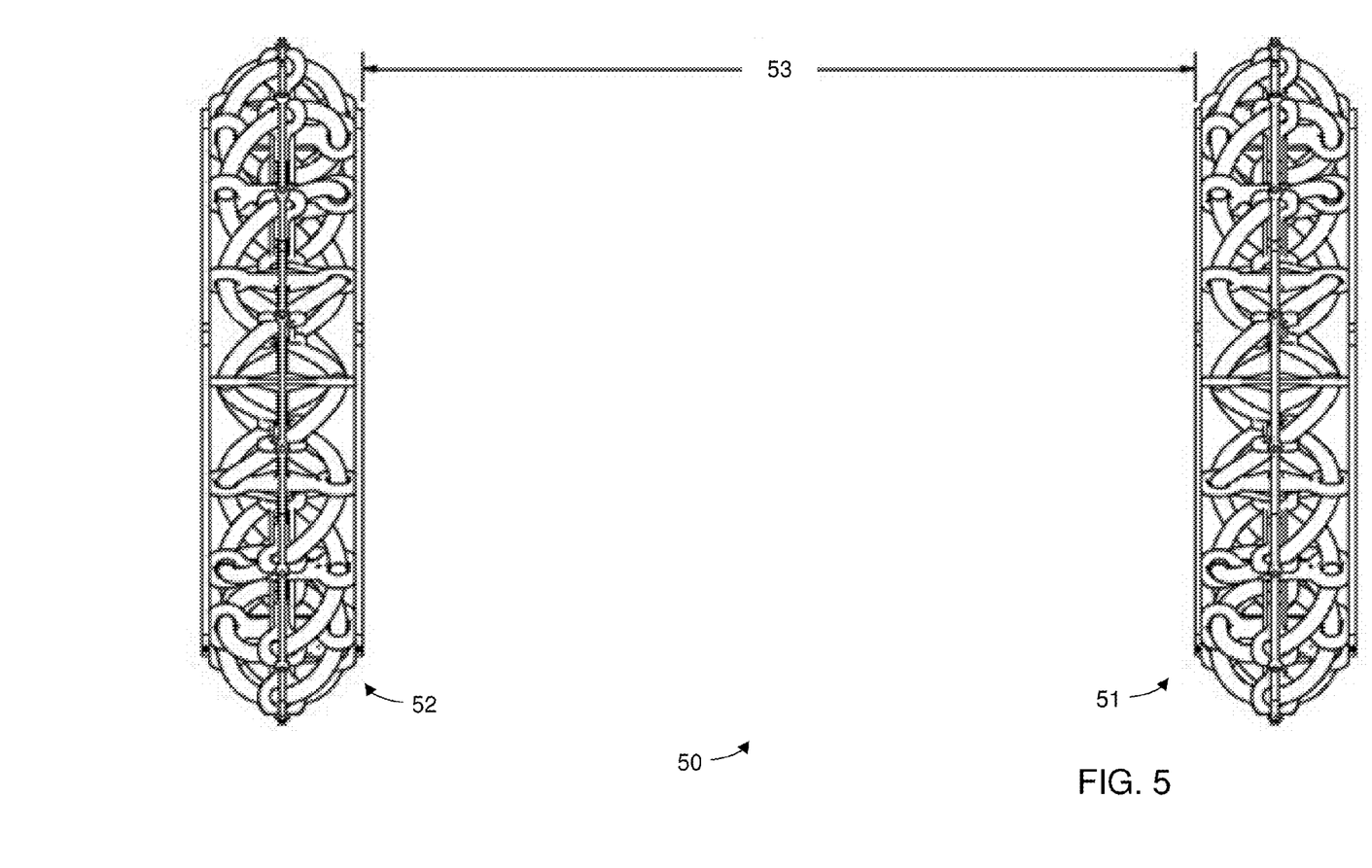
FIG. 5 illustrates an arrangement of two exemplary bodies that each include two intertwined helically wound runners.

FIG. 5 illustrates an exemplary system 50 that includes an arrangement of two exemplary bodies 51 and 52 that each include two intertwined helically wound runners. In some implementations, body 51 may be similar to body 40 shown in FIG. 4. By way of non-limiting example, components shown in FIG. 4 may be included in system 50 (as well as system 60 in FIG. 6, system 70 in FIG. 7, and system 80 in FIG. 8, and vice versa), such as a first runner, a second runner, one or more support structures, a first twisted conductive wire wound around the first runner, a second twisted conductive wire wound around the second runner, a first connector, a second connector, one or more power sources and/or current sources, and/or other components. By way of non-limiting example, this disclosure envisions combining elements shown in different figures.

Referring to FIG. 5, in some implementations, body 52 may be similar to body 40 shown in FIG. 4. Referring to FIG. 5, body 51 and body 52 may be arranged such that the first plane that bisects the toroidal shape of body 51 and the second plane that bisects the toroidal shape of body 52 are parallel to each other. In some implementations, body 51 and body 52 may be arranged such that the axis through the hole (not shown due to viewpoint) of the toroidal shape of body 51 (as described in relation to FIG. 1) is aligned with the axis through the hole (not shown due to viewpoint) of the toroidal shape of body 52.

In some implementations, body 51 and body 52 may be arranged a distance 53 apart. In some implementations, distance 53 may be about 4 inches, about 6 inches, about 1 foot, about 18 inches, about 2 feet, about 30 inches, about 3 feet, about 4 feet, about 5 feet, about 6 feet, about 7 feet, about 8 feet, about 9 feet, about 10 feet, and/or other distances.

In some implementations, the double helix of body 51 may have the opposite handedness as the double helix of body 52. In some implementations, the double helix of body 51 may have the same handedness as the double helix of body 52.

Figure 6:
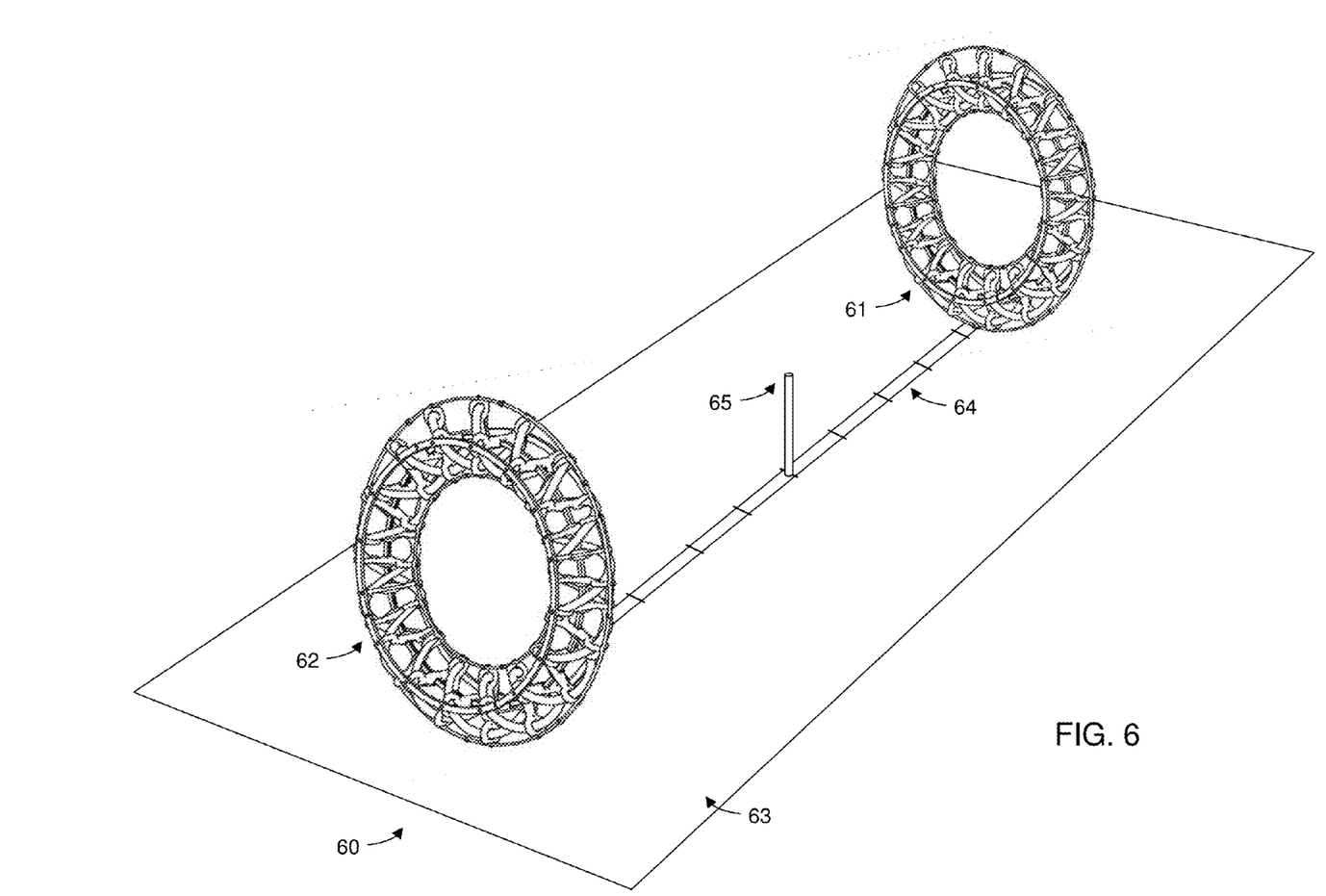
FIG. 6 illustrates an arrangement of two exemplary bodies that each include two intertwined helically wound runners.

FIG. 6 illustrates an exemplary system 60 that includes an arrangement of two exemplary bodies 61 and 62 that each include two intertwined helically wound runners. In some implementations, body 61 may be similar to body 51 shown in FIG. 5 and/or body 40 shown in FIG. 4. In some implementations, body 62 may be similar to body 52 shown in FIG. 5 and/or body 40 shown in FIG. 4. Referring to FIG. 6, body 61 and body 62 may be arranged on a surface or structure 63, e.g. a tabletop. In some implementations, system 60 may include a support structure 64 configured to adjustably support body 61 and/or body 62 such that a distance between body 61 and body 62 may be adjustable. In some implementations, support structure 64 may include a track. In some implementations, body 61 and/or body 62 may be supported by and/or mounted on support structure 64. In some implementations, system 60 may include a support structure 65 configured to support an object, an organism, a sample, tissue, stem cells, living cells, and/or any other (organic) matter that may benefit from being subjected to an electromagnetic effect generated by system 60. In some implementations, such matter may be placed on support structure 65, e.g. on the top of support structure 65. By way of non-limiting example, a petri dish may be placed on support structure 65. In some implementations, the petri dish may contain samples of planarian that are being treated by being subjected to an electromagnetic effect generated by system 60. Experiments have shown that a severed tail of a planarian may be regenerated in about 16 hours, as opposed to multiple days (or even a few weeks) without being treated.

In some implementations, system 60 may include one or more other support structures having a similar functionality as support structure 65, but arranged and/or disposed in different positions relative to body 61 and/or body 62. The arrangement shown in FIG. 6 is merely exemplary and not intended to be limiting.

In some implementations, body 61 and body 62 may be arranged such that the first plane that bisects the toroidal shape of body 61 and the second plane that bisects the toroidal shape of body 62 are parallel to each other. In some implementations, body 61 and body 62 may be arranged such that the axis through the hole of the toroidal shape of body 61 is aligned with (e.g. in the same three-dimensional position as) the axis through the hole of the toroidal shape of body 62.

Figure 7:
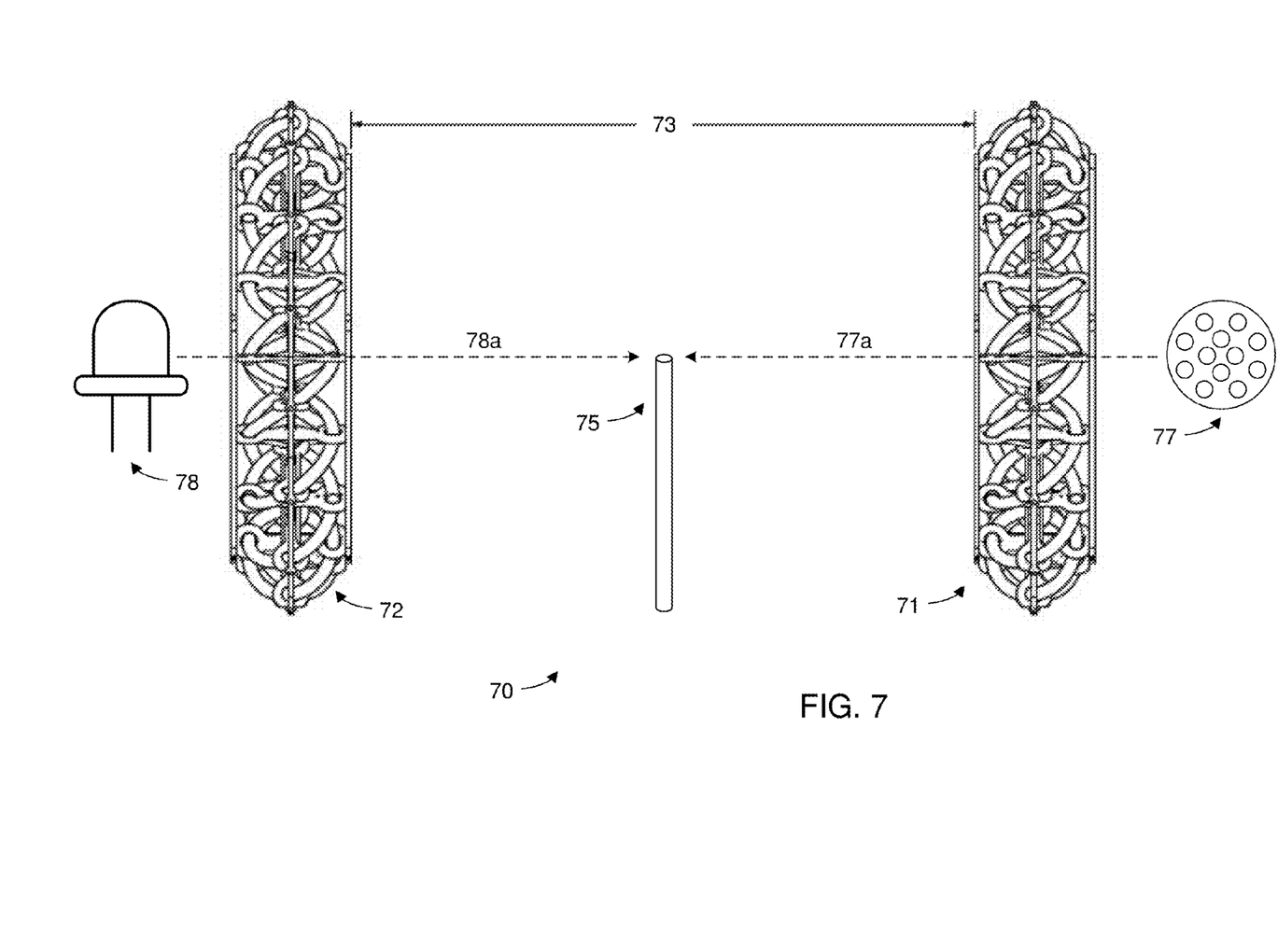
FIG. 7 illustrates an arrangement of multiple light sources and two exemplary bodies that each include two intertwined helically wound runners.

FIG. 7 illustrates an exemplary system 70 that includes an arrangement of multiple light sources 77 and 78 and two exemplary bodies 71 and 72 that each include two intertwined helically wound runners. In some implementations, body 71 may be similar to body 61 shown in FIG. 6, body 51 shown in FIG. 5, and/or body 40 shown in FIG. 4. In some implementations, body 72 may be similar to body 62 shown in FIG. 6, body 52 shown in FIG. 5, and/or body 40 shown in FIG. 4. Referring to FIG. 7, body 71 and body 72 may be arranged such that the first plane that bisects the toroidal shape of body 71 and the second plane that bisects the toroidal shape of body 72 are parallel to each other. In some implementations, body 71 and body 72 may be arranged such that the axis through the hole (not shown due to viewpoint) of the toroidal shape of body 71 (as described in relation to FIG. 1) is aligned with the axis through the hole (not shown due to viewpoint) of the toroidal shape of body 72.

In some implementations, body 71 and body 72 may be arranged a distance 73 apart. In some implementations, distance 73 may be about 4 inches, about 6 inches, about 1 foot, about 18 inches, about 2 feet, about 30 inches, about 3 feet, about 4 feet, about 5 feet, about 6 feet, about 7 feet, about 8 feet, about 9 feet, about 10 feet, and/or other distances.

In some implementations, system 70 may include a support structure 75 configured to support an object, an organism, a sample, tissue, stem cells, living cells, and/or any other (organic) matter that may benefit from being subjected to an electromagnetic effect generated by system 70. In some implementations, such matter may be placed on support structure 75, e.g. on the top of support structure 75. In some implementations, system 70 may include one or more other support structures having a similar functionality as support structure 75, but arranged and/or disposed in different positions relative to body 71 and/or body 72. The arrangement shown in FIG. 7 is merely exemplary and not intended to be limiting. Support structure 75 may be similar to support structure 65 shown in FIG. 6.

In some implementations, system 70 may include light source 77, light source 78, and/or other sources of electromagnetic radiation. In some implementations, light source 77 may be arranged and/or disposed in proximity of body 71. In some implementations, light source 78 may be arranged and/or disposed in proximity of body 72. In some implementations, light source 78 may emit a narrow spectrum of electromagnetic radiation. For example, light source 78 may include a laser and/or another light source that emits a narrow spectrum of electromagnetic radiation. In some implementations, light source 78 may be configured to be pulsed at a particular frequency, e.g., synchronized with one or more frequencies used to supply alternating current to the twisted wires wound around the runners of a body. In some implementations, light source 78 may be configured to be pulsed at a particular frequency, e.g., the beat frequency that is created as described in this disclosure. In some implementations, light source 78 may be configured to be pulsed using a sine wave, a square wave, and/or another type of control. In some implementations, light source 78 may be configured to be pulsed using different duty cycles, e.g., 50/50, 40/60, 30/70, 20/80, 10/90, and/or another duty cycle. In some implementations, the addition of one or more light sources reduced the regeneration period of certain organic matter or organisms (e.g. planarians) by 25% (e.g. from 24 hours to 18 hours).

In some implementations, a filter (not shown) having a narrow bandwidth may be placed between light source 78 and body 72 such that electromagnetic radiation emitted by light source 78 (at least along direction 78a as shown in FIG. 7, and/or in other directions) passes through the filter prior to traversing through body 72 and/or impinging on any matter and/or object, such as support structure 75, that is disposed between body 72 and body 71. In some implementations, light source 77 may emit a narrow spectrum of electromagnetic radiation. For example, light source 77 may include one or more light emitting diodes (LEDs) and/or another light source that emits a narrow spectrum. In some implementations, a filter (not shown) having a narrow bandwidth may be placed between light source 77 and body 71 such that electromagnetic radiation emitted by light source 77 (at least along direction 77a as shown in FIG. 7, and/or in other directions) passes through the filter prior to traversing through body 71 and/or impinging on any matter and/or object, such as support structure 75, that is disposed between body 72 and body 71. In some implementations, one or more filters may be disposed in proximity of support structure 75 such that electromagnetic radiation emitted by one or more light sources passes through one or more filters prior to impinging on any matter and/or object that is supported by support structure 75.

In some implementations, system 70 may include multiple similar light sources. For example, system 70 may include two light sources that are similar to light source 77, or two light sources that are similar to light source 78, and/or two light sources that are similar to each other. Referring to FIG. 7, the illustration of light source 78 and light source 78 in FIG. 7 is merely schematic, and not intended to be limiting with regard to the functionality of the light sources.

Figure 8:
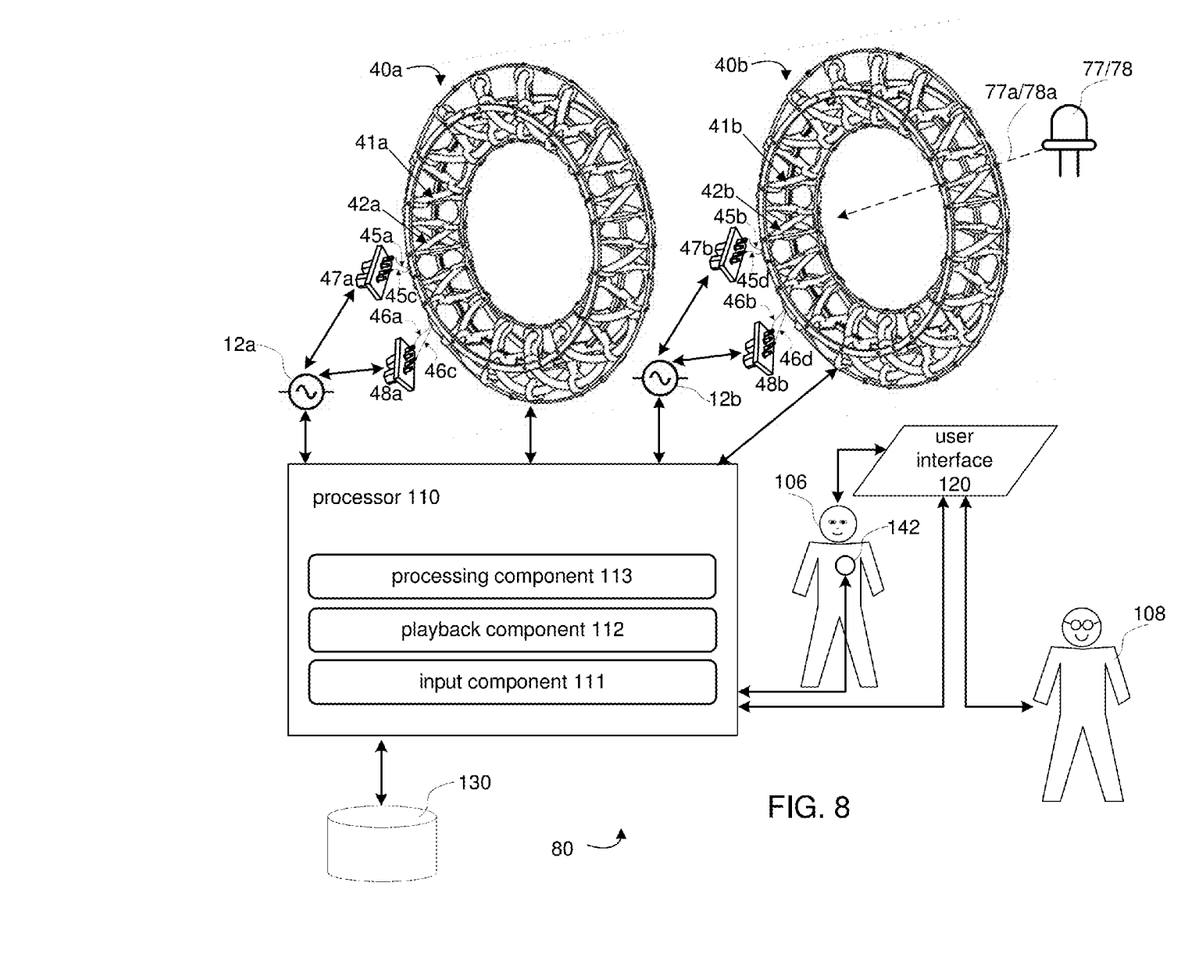
FIG. 8 illustrates a system that includes two exemplary bodies that each include two intertwined helically wound runners.

FIG. 8 illustrates an exemplary system 80 that includes one or more of a processor 110, a user interface 120, electronic storage, connectors 47a, 47b, 48a, and 48b, power sources 12a and 12b, light sources 77 and 78, bodies 40a and 40b that each including two intertwined helically wound runners sharing the same circular axis, both runners having conductive wires spirally wound therearound. System 80 may include body 40a. In some implementations, body 40a may be similar to body 40 shown in FIG. 4. Body 40a may include a first runner 41a and a second runner 42a. A first conductive twisted wire may be wound around first runner 41a and electrically coupled to connector 47a via twisted wire ends 45a and 45c. A second conductive twisted wire may be wound around second runner 42a and electrically coupled to connector 48a via twisted wire ends 46a and 46c. Connectors 47a and 48a may be electrically coupled to power source 12a such that one or more electric currents are supplied to the twisted wires wound around first runner 41a and second runner 42a, such that an electromagnetic effect (e.g. an electromagnetic field) is created around and/or near body 40a. System 80 may include body 40b. In some implementations, body 40b may be similar to body 40 shown in FIG. 4. Body 40b may include a first runner 41b and a second runner 42b. A first conductive twisted wire may be wound around first runner 41b and electrically coupled to connector 47b via twisted wire ends 45b and 45d. A second conductive twisted wire may be wound around second runner 42b and electrically coupled to connector 48b via twisted wire ends 46b and 46d. Connectors 47b and 48b may be electrically coupled to power source 12b such that one or more electric currents are supplied to the twisted wires wound around first runner 41b and second runner 42b, such that an electromagnetic effect (e.g. an electromagnetic field) is created around and/or near body 40b. In some implementations, power may be supplied to connectors 47a, 47b, 48a, and 48b via a single power source. In some implementations, electromagnetic radiation may be emitted by light sources 77 and/or 78, e.g. along direction 77a and/or 78a. In some implementations, electromagnetic radiation may be emitted by a single light source. In some implementations, one or more light sources of system 80 may have a similar structure and/or similar features as described in any other system herein, including but not limited to system 70 in FIG. 7.

Regarding systems 40, 50, 60, 70, and 80, any two intertwined helically wound runners may share the same axis, be congruent, and/or differ by a translation along the axis, e.g. measuring half the pitch.

By way of non-limiting example, additional structures and/or features of any bodies in systems 40, 50, 60, 70, and 80 may be described in U.S. Pat. No. 8,653,925, entitled "Double Helix Conductor," which issued Feb. 18, 2014, which is hereby incorporated into this disclosure by reference in its entirety. This patent may also be referred to as "the '925 patent" herein.

The runners in systems 40, 50, 60, 70, and 80 may be manufactured from one or more of plastic, plastic plated with metals including copper, nickel, iron, soft iron, nickel alloys, fiberoptic materials, and/or other materials (or combinations thereof). In some implementations, one or more runners may be are manufactured from non-conductive material.

The number of turns of a set of twisted wires per inch and/or per helical revolution of a runner may be characteristic measurements/features of an implementation of any of the systems described herein. In some implementations, the number of twists per inch of a twisted wire may be about 2, about 5, about 10, about 20, about 50, about 100, about 150, about 200, about 250, and/or another suitable number of twists. In some implementations, the frequency characteristics of an alternating current and/or the corresponding generated electromagnetic effect or field may be based on, proportional to, and/or otherwise related to the number of twists of a twisted wire. For example, a higher number of twists per inch may correspond to a higher operating frequency for the alternating current and/or the corresponding generated electromagnetic effect and/or field. In some implementations, multiple twisted wires (e.g. a first twisted wire wound around a first runner and a second twisted wire wound around a second runner) may have the same direction of twisting, and/or a different direction of twisting. In some implementations, multiple wires (e.g. twisted wires) may be wound around the same runner. In some implementations, a wire may be wound around some or all of one or more struts.

The electric currents supplied to the conductive wires wound around the first and second runner of any of the bodies in systems 40, 50, 60, 70, and 80 may flow in the same direction or the opposite direction. For alternating currents, operating frequencies ranging from more than 0 Hz to about 40 GHz are contemplated. The operating frequencies for the conductive wires wound around the first and second runner of any of the bodies in systems 40, 50, 60, 70, and 80 may be the same or different. Other electrical operating characteristics of the supplied currents, such as phase, amplitude, power-level, and/or other operating characteristics, may be the same or different. Systems 40, 50, 60, 70, and 80 may be used to exploit the electromagnetic field that is created when electrical power is supplied to one or more wires of one or more bodies.

Referring to FIG. 7, the electromagnetic radiation emitted by one or both of light sources 77 and 78 may include specific wavelengths. By virtue of using specific wavelengths, emitted electromagnetic radiation may produce specific biological effects. This biophysical principle may be referred to as photo-bio-modulation. In some implementations, the emitted electromagnetic radiation may interact with a flow of energy of a subject 106 (shown in FIG. 8).

In some implementations, the conductive wires wound around the first and second runner of body 40a are supplied with a first alternating current, e.g. of 216 Hz, and the conductive wires wound around the first and second runner of body 40b are supplied with a second alternating current, e.g., of 864 Hz. In some implementations, the currents supplied to body 40a and body 40b may be 180 degrees out of phase. Supply of the first and second current may create a beat frequency of 432 Hz (corresponds to an "A" note). In some implementations, using a similar approach, beat frequencies of 486 Hz, 512 Hz, 576 Hz, 648 Hz, 729 Hz, 768 Hz, and/or other frequencies may be used, which correspond to "B," "C," "D," "E," "F," and "G" notes, respectively. In some implementations, the double helix of body 40a may have the opposite handedness as the double helix of body 40b. In some implementations, the double helix of body 40a may have the same handedness as the double helix of body 40b.

In some implementations, by combining elements of FIG. 7 and FIG. 8, the one or more light sources may be configured to emit electromagnetic radiation that predominantly includes visible wavelengths. Particular wavelengths may be selected to correspond (and be supplied contemporaneously) with particular beat frequencies. For example, the combination of using a beat frequency of 432 Hz and one or more light sources emitting electromagnetic radiation having a predominant wavelength of 631 nm has been found useful in various applications. Other useful combinations include 486 Hz and 561 nm, 512 Hz and 533 nm, 576 Hz and 473 nm, 648 Hz and 421 nm, 729 Hz and 748 nm, and 768 Hz and 710 nm. These examples are not intended to be limiting. As used herein, the term "predominant wavelength" may refer to emission of electromagnetic radiation wherein at least 50% of the emitted energy has a particular wavelength. For example, a light source emitting a predominant wavelength of 631 nm may be interpreted as a light source emitting electromagnetic radiation wherein at least 50% of the emitted energy is within 5%, 4%, 3%, 2%, 1%, and/or another percentage of a particular wavelength, such as, by way of non-limiting example, 631 nm. For example, the term "within 5% of 631 nm" may be interpreted as "between 95% of 631 nm and 105% of 631 nm," or, roughly, between 600 nm and 663 nm. Likewise, the term "within 1% of 631 nm" may be interpreted as "between 99% of 631 nm and 101% of 631 nm," or, roughly, between 625 nm and 638 nm.

Any combination of one or more generated electromagnetic effects (e.g. an electromagnetic effect and/or field generated as described in this disclosure), emitted electromagnetic radiation, and/or biological effects produced by virtue of proximity (as described in this disclosure) may be used to provide therapy to a subject.

Applications for any of the systems described herein may include affecting growth and/or growth rate of plants, livestock, samples, tissue, stem cells, living cells, and/or other (organic) matter, medical applications, therapeutic applications, energy production, energy conversion, energy transformation, adenosine triphosphate (ATP) production, ATP transfer, ATP processing, and/or other applications.

In some implementations, a system including any of the components shown in FIGS. 4-8 (and/or multiple instances thereof) may be used as a component in an electrical circuit, performing one or more functions and/or applications including a (tunable) inductor, a (Tesla) coil, a transformer, a transducer, a transistor, a resistor, a solenoid, a stator for an electrical motor, an electromagnet, an electromagnetic pulse generator, an electromagnetic actuator, an energy conversion device, a position servomechanism, a generator, a stepping motor, a DC motor, a (contact-free) linear drive, an axial flux device, a measurement device for magnetic permeability, a dipole magnet, a device to alter electron and/or particle trajectory, and/or any combination thereof.

Referring to FIG. 8, system 80 may include one or more of user interface 120, one or more physical processors 110, one or more sensors 142, electronic storage 130, one or more power sources and/or current sources (e.g. power source 12a and power source 12b), one or more light sources (e.g. light source 77 and/or light source 78), an input component 111, a playback component 112, a processing component 113, and/or other components.

Sensor(s) 142 may be configured to generate output signals conveying information. The information may include electrophysiological information and/or other information. In some implementations, the one or more sensors 142 may include one or more of an audio sensor, a microphone, a stethoscope, a pressure sensor, a motion sensor, a proximity sensor, an electromagnetic sensor, an electrode, a temperature sensor, a current sensor, an optical sensor, an electro-optical sensor, and/or other sensors or combinations thereof. In some implementations, the one or more processors 110 may be configured to provide information-processing capabilities and/or execute computer program components, including but not limited to input component 111, playback component 112, processing component 113, and/or other components. By way of non-limiting example, additional structures and/or features of sensor 142, processor 110, user interface 120, electronic storage 130, input component 111, playback component 112, and/or processing component 113, may be described in U.S. patent application Ser. No. 14/194,412, entitled "Health Applications for Using Bio-Feedback to Control an Electromagnetic Field," which was filed Feb. 28, 2014, which is hereby incorporated into this disclosure by reference in its entirety. This application may also be referred to as "the '412 application" herein.

In some implementations, one or more currents supplied to connectors 47a, 47b, 48a, and 48b may correspond to one or more sensor-generated output signals. In some implementations, the one or more currents may correspond to one or more signals generated by a transducer and/or one or more other components of system 80. In some implementations, an alternating current supplied to body 40a and/or 40b may include a carrier signal and a modulating signal. In some implementations, carrier signals used for the alternating current may be radio-frequency signals. As used herein, radio frequency may refer to frequencies between about 30 kHz and about 30 GHz. In some implementations, the modulating signal for the alternating current may be modulated through one or more of amplitude modulation, frequency modulation, phase modulation, digital modulation, and/or other types of modulation.

In some implementations, the one or more frequencies included in an alternating current supplied to body 40a and/or 40b may be based on audio recordings of a note, tone, or chord, generated by a frequency generator and/or a (musical) instrument. For example, a first frequency may be based on the sound of a piano playing an A above middle C (also referred to as A4, which may include sound having a frequency of about 432 Hz, depending on the tuning system used). For example, a second frequency may be based on the sound of some instrument (e.g. a piano) playing a note forming a harmonious interval with A4, which may include sound having a frequency of about 648 Hz. This tuning may be referred to as Pythagorean tuning. Mathematically perfect tuning may combine notes having a 3:2 ratio. Different types of tuning (or tuning systems), including but not limited to equal tempered tuning, may be used and considered within the scope of this disclosure.

In some implementations, electromagnetic radiation emitted by one or more light sources 77 and/or 78 may correspond to one or more sensor-generated output signals. In some implementations, the one or more predominant wavelengths of the electromagnetic radiation emitted by one or more light sources 77 and/or 78 may be based on audio recordings of a note, tone, or chord, generated by a frequency generator and/or a (musical) instrument.

Processor 110 may include one or more of a digital processor, an analog processor, a digital circuit designed to process information, a central processing unit, a graphics processing unit, an analog circuit designed to process information, and/or other mechanisms for electronically processing information. Although processor 110 is shown in FIG. 8 as a single entity, this is for illustrative purposes only. In some implementations, processor 110 may include a plurality of processing units.

It should be appreciated that although components 111-113 are illustrated in FIG. 8 as being co-located within a single processing unit, in implementations in which processor 110 includes multiple processing units, one or more of components 111-113 may be located remotely from the other components. The description of the functionality provided by the different components 111-113 described herein is for illustrative purposes, and is not intended to be limiting, as any of components 111-113 may provide more or less functionality than is described. For example, one or more of components 111-113 may be eliminated, and some or all of its functionality may be incorporated, shared, integrated into, and/or otherwise provided by other ones of components 111-113. Note that processor 110 may be configured to execute one or more additional components that may perform some or all of the functionality attributed below to one of components 111-113.

Input component 111 may be configured to obtain information, e.g. from one or more digital audio files, or, alternatively and/or simultaneously, based on sensor-generate output signals. In some implementations, the information may be obtained from storage, e.g. from electronic storage. Information obtained from storage may include electronic audio files in any format, including but not limited to MP3, WMA, WAV, AIFF, and/or other audio formats. In some implementations, information may be obtained from sound sources including frequency generators, phonographs, CD-players, DVD players, AM radio, FM radio, and/or other sound sources.

Processing component 113 may be configured to process the obtained information from input component 111. In some implementations, processing component 113 may be configured to generate a processed signal based on the obtained information from input component 111. For example, processing component 113 may convert, filter, modify, and/or otherwise transform information or signals from input component 111 to generate the processed signal.

Playback component 112 may be configured to produce sound signals based on one or more of the obtained information from input component 111 and/or the processed signal from processing component 113. The sound signals produced by playback component 112 may be coupled electrically to the leads/ends of one or more conductive wires wound around one or more runners of body 40a and/or 40b such that the induced current corresponds to and/or is based on the sound signals. Alternatively, and/or simultaneously, the induced current may be controlled by and/or based on the sound signals produced by playback component 112. In some implementations, the sound signals produced by playback component 112 may be amplified by an amplifier before being electrically coupled to the leads/end of one or more conductive wires. In some preferred implementations, the amplifier may be an audio amplifier ranging between 100 W and 400 W. Other types of amplifiers and/or amplifiers having a different power range are also contemplated.

Electronic storage 130 in FIG. 8 comprises electronic storage media that electronically stores information. The electronic storage media of electronic storage 130 may include one or both of system storage that is provided integrally (i.e., substantially non-removable) with system 80 and/or removable storage that is connectable to system 80 via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 80 to function properly. For example, electronic storage 130 may store sound information and/or electronic audio files (as discussed elsewhere herein), and/or other information. Electronic storage 130 may be a separate component within system 80, or electronic storage 130 may be provided integrally with one or more other components of system 80 (e.g., processor 110).

User interface 120 of system 80 in FIG. 8 is configured to provide an interface between system 80 and a user (e.g., a user 108, a subject 106, a caregiver, a therapy decision-maker, etc.) through which the user can provide information to and receive information from system 80. This enables data, results, and/or instructions and any other communicable items, collectively referred to as "information," to be communicated between the user and system 80. An example of information that may be conveyed to user 108 is an indication of the volume and/or intensity of the sound signals produced by playback component 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 80 from removable storage (e.g., a smart card, a flash drive, a removable disk, etc.) that enables the user(s) to customize system 80. Other exemplary input devices and techniques adapted for use with system 80 as user interface 120 include, but are not limited to, an RS-232 port, RF link, an IR link, modem (telephone, cable, Ethernet, internet or other). In short, any technique for communicating information with system 80 is contemplated as user interface 120.

Figure 9:
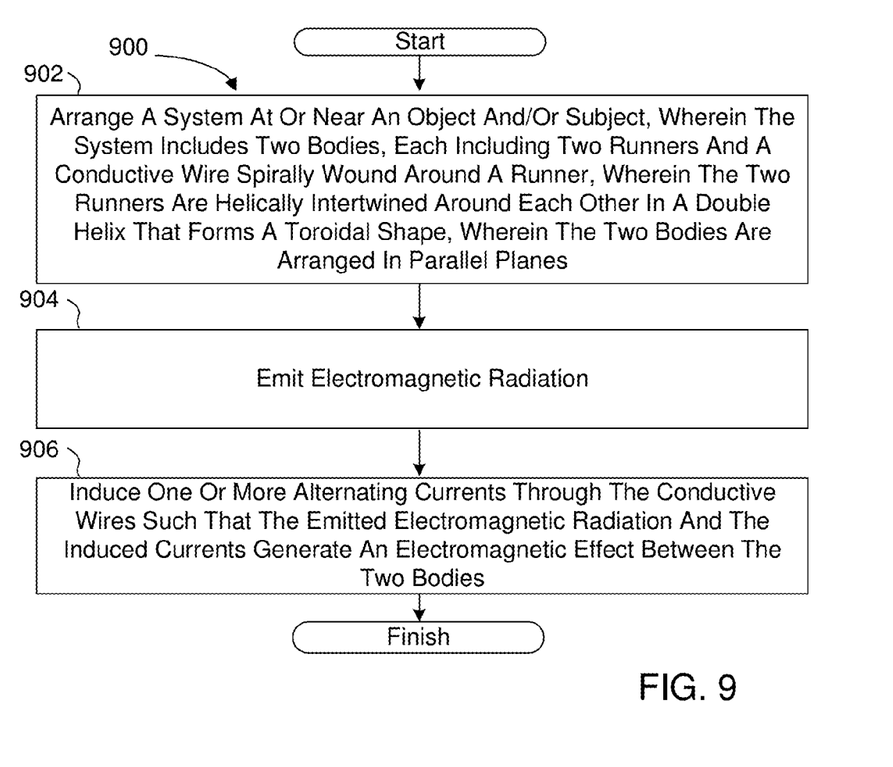
FIG. 9 illustrates a method for providing therapy to a subject or promoting growth, according to one or more implementations.

FIG. 9 illustrates a method 900 for providing therapy and/or electromagnetic effects to an object and/or a subject. The operations of method 900 presented below are intended to be illustrative. In certain implementations, method 900 may be accomplished with one or more additional operations not described, and/or without one or more of the operations discussed. Additionally, the order in which the operations of method 900 are illustrated in FIG. 9 and described below is not intended to be limiting.

In certain implementations, method 900 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

Regarding method 900, at an operation 902, a system is arranged at or near one or both of an object and a subject. The system includes a first body and a second body. The first body includes a first runner, a second runner, and a first conductive wire. The first runner and the second runner are helically intertwined around each other in a double helix that forms a first toroidal shape having a first center. The first toroidal shape is bisected by a first plane that includes the first center and divides the first toroidal shape into two similar halves. The first conductive wire is spirally wound around the first runner. The second body includes a third runner, a fourth runner, and a second conductive wire. The third runner and the fourth runner are helically intertwined around each other in a second double helix that forms a second toroidal shape having a second center. The second toroidal shape is bisected by a second plane that includes the second center and divides the second toroidal shape into two similar halves. The second conductive wire is spirally wound around the third runner. The first body and the second body are arranged such that the first plane is parallel to the second plane. In some embodiments, operation 902 is performed by a system the same as or similar to system 80 (shown in FIG. 8 and described herein).

At an operation 904, electromagnetic radiation is emitted. In some embodiments, operation 904 is performed by one or more light sources the same as or similar to light sources 77 and 78 (shown in FIG. 8 and described herein).

At an operation 906, one or more alternating currents are induced through the first conductive wire and the second conductive wire such that the one or more alternating currents and the emitted electromagnetic radiation generate an electromagnetic effect at or near the object and/or the subject. In some embodiments, operation 906 is performed by one or more power sources the same as or similar to power sources 12a and 12b (shown in FIG. 8 and described herein).

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system comprising:
   a first body including:
      a first runner and a second runner that are intertwined and helically wound around each other in a double helix that forms a first toroidal shape comprising a first center, wherein the first toroidal shape is bisected by a first plane that includes the first center and divides the first toroidal shape into two halves; and a first conductive wire spirally wound around the first runner;
   a second body including:
      a third runner and a fourth runner that are intertwined and helically wound around each other in a second double helix that forms a second toroidal shape comprising a second center, wherein the second toroidal shape is bisected by a second plane that includes the second center and divides the second toroidal shape into two halves; and
      a second conductive wire spirally wound around the third runner;
   one or more current sources that provide one or more alternating currents to the first conductive wire and the second conductive wire; and
   one or more light sources configured to emit electromagnetic radiation,
   wherein the first body and the second body are arranged such that the first plane is parallel to the second plane, and
   wherein the system is configured to generate an electromagnetic effect responsive to the one or more alternating currents being provided, and further responsive to the electromagnetic radiation being emitted.

2. The system of claim 1, wherein the first body and the second body are further arranged such that a line through the first center and the second center is perpendicular to the first plane and to the second plane.

3. The system of claim 1, wherein the first conductive wire includes a first set of twisted wires, and wherein the second conductive wire includes a second set of twisted wires.

4. The system of claim 1, wherein the first body further includes a third conductive wire spirally wound around the second runner, wherein the second body further includes a fourth conductive wire spirally wound around the fourth runner, and wherein the one or more current sources further provide one or more alternating currents to the third conductive wire and the fourth conductive wire.

5. The system of claim 1, further comprising a first carrying structure configured to carry the first body, a second carrying structure configured to carry the second body, and a support structure configured to adjustably support the first and second carrying structures such that a distance between the first body and the second body is adjustable by adjusting a point of engagement between the first carrying structure and the support structure.

6. The system of claim 1, wherein the system is further configured to be arranged in proximity of organic matter, wherein the electromagnetic effect promotes one or both of growth and regeneration of the organic matter at one or more locations between the first and second body.

7. The system of claim 1, wherein the system is further configured to provide therapy to a subject in proximity to the system, wherein the therapy is provided through the generated electromagnetic effect.

8. The system of claim 1, wherein the first conductive wire is spirally wound around.

9. The system of claim 1, wherein the double helix of the first body comprises a diameter between 4 inches and 10 feet.

10. The system of claim 1, wherein the first body and the second body are arranged between 4 inches and 10 feet apart.

11. The system of claim 1, wherein the one or more alternating currents comprise frequencies between 20 Hz and 20 kHz.

12. The system of claim 1, wherein a first alternating current provided to the first conductive wire comprises a frequency of 216 Hz, and wherein a second alternating current provided to the second conductive wire comprises a frequency of 864 Hz.

13. The system of claim 1, wherein the electromagnetic effect includes an electromagnetic field.

14. The system of claim 1, wherein the one or more light sources include one or more light emitted diodes (LEDs), wherein the one or more LEDs include a light emitting diode configured to predominantly emit electromagnetic radiation comprising a wavelength of 631 nm.

15. The system of claim 1, further comprising:
   one or more physical processors configured via computer-readable instructions to:
      obtain information that includes one or more digital audio files;
      process the obtained information and generate a processed signal based on the obtained information, and
      produce sound signals based on the processed signal, wherein the one or more alternating currents are dynamically controlled to correspond to the produced sound signals such that one or more frequencies of the one or more alternating currents correspond to one or more frequencies of the produced sound signals.

16. A method for providing electromagnetic effects, the method comprising:
   arranging a system at or near one or both of an object and a subject, wherein the system includes a first body, a second body and one or more light sources,
      wherein the first body includes a first runner, a second runner, and a first conductive wire,
         wherein the first runner and the second runner are helically intertwined around each other in a double helix that forms a first toroidal shape comprising a first center,
         wherein the first toroidal shape is bisected by a first plane that includes the first center and divides the first toroidal shape into two halves,
         wherein the first conductive wire is spirally wound around the first runner,
      wherein the second body includes a third runner, a fourth runner, and a second conductive wire,
         wherein the third runner and the fourth runner are helically intertwined around each other in a second double helix that forms a second toroidal shape comprising a second center,
         wherein the second toroidal shape is bisected by a second plane that includes the second center and divides the second toroidal shape into two halves,
         wherein the second conductive wire is spirally wound around the third runner, and,
      wherein the first body and the second body are arranged such that the first plane is parallel to the second plane;
   emitting electromagnetic radiation via said one or more light sources; and inducing one or more alternating currents through the first conductive wire and the second conductive wire such that the one or more alternating currents and the emitted electromagnetic radiation generate an electromagnetic effect at or near the object and/or the subject.

17. The method of claim 16, wherein the first body and the second body are further arranged such that a line through the first center and the second center is perpendicular to the first plane and to the second plane.

18. The method of claim 16, wherein the first conductive wire includes a first set of twisted wires, and wherein the second conductive wire includes a second set of twisted wires.

19. The method of claim 16, wherein the first body further includes a third conductive wire spirally wound around the second runner, wherein the second body further includes a fourth conductive wire spirally wound around the fourth runner, the method further comprising: providing one or more alternating currents to the third conductive wire and the fourth conductive wire.

20. The method of claim 16, further comprising: arranging a first carrying structure to carry the first body; arranging a second carrying structure to carry the second body; and arranging a support structure to adjustably support the first and second carrying structures such that a distance between the first body and the second body is adjustable by adjusting a point of engagement between the first carrying structure and the support structure.

21. The method of claim 16, wherein the object includes organic matter, the method further comprising promoting one or both of growth and regeneration of the organic matter at one or more locations between the first and second body.

22. The method of claim 16, the method further comprising: providing therapy to the subject in proximity to the system, wherein the therapy is provided through the generated electromagnetic effect.

23. The method of claim 16, wherein the first conductive wire is spirally wound around the first runner between 10 and 1000 revolutions per inch of the first runner.

24. The method of claim 16, wherein the double helix of the first body comprises a diameter between 4 inches and 10 feet.

25. The method of claim 16, wherein the first body and the second body are arranged between 4 inches and 10 feet apart.

26. The method of claim 16, wherein the one or more alternating currents comprise frequencies between 20 Hz and 20 kHz.

27. The method of claim 16, wherein a first alternating current provided to the first conductive wire comprises a frequency of 216 Hz, and wherein a second alternating current provided to the second conductive wire comprises a frequency of 864 Hz.

28. The method of claim 16, wherein the electromagnetic effect includes an electromagnetic field.

29. The method of claim 16, wherein the one or more light sources include one or more light emitted diodes (LEDs), wherein the one or more LEDs include a light emitting diode configured to predominantly emit electromagnetic radiation comprising a wavelength of 631 nm.

30. The method of claim 16, further comprising:
obtaining information that includes one or more digital audio files;
processing the obtained information and generating a processed signal based on the obtained information, and
producing sound signals based on the processed signal,
wherein the one or more alternating currents are dynamically controlled to correspond to the produced sound signals such that one or more frequencies of the one or more alternating currents correspond to one or more frequencies of the produced sound signals.

* * * * *